(12) United States Patent
Binder

(10) Patent No.: US 6,684,107 B1
(45) Date of Patent: Jan. 27, 2004

(54) WRINKLE-REDUCING SYSTEM

(75) Inventor: Gary Binder, Portland, OR (US)

(73) Assignee: Voyager Medical Corporation, Portland, OR (US)

( * ) Notice: Subject to any disclaimer, the term of this patent is extended or adjusted under 35 U.S.C. 154(b) by 193 days.

(21) Appl. No.: 09/920,550

(22) Filed: Aug. 1, 2001

(51) Int. Cl.⁷ .............................................. A61N 1/18
(52) U.S. Cl. ....................................... 607/72; 607/145
(58) Field of Search .......................... 607/48, 50, 72, 607/74, 76, 115, 149, 145, 150

(56) References Cited

U.S. PATENT DOCUMENTS

| | | |
|---|---|---|
| 3,866,600 A | 2/1975 | Rey |
| 3,911,909 A | 10/1975 | Di Matteo |
| 4,233,986 A | 11/1980 | Tannenbaum |
| 4,522,210 A * | 6/1985 | Simonin ..................... 128/421 |
| 4,694,840 A | 9/1987 | Kairis et al. |
| 4,769,881 A | 9/1988 | Pedigo et al. |
| 4,926,880 A | 5/1990 | Claude et al. |
| 4,957,480 A * | 9/1990 | Morenings ................... 604/20 |
| 4,982,742 A | 1/1991 | Claude |
| 4,982,743 A | 1/1991 | Pierson |
| 5,012,816 A * | 5/1991 | Lederer ....................... 128/735 |
| 6,155,966 A * | 12/2000 | Parker ......................... 600/13 |
| 6,249,706 B1 * | 6/2001 | Sobota et al. ............... 607/115 |

OTHER PUBLICATIONS

Walter R. Gault, MSPH, and Paul F. Gatens, Jr., MD, "Use of Low Intensity Direct Current in Management of Ischemic Skin Ulcers," Physical Therapy, vol. 56, No. 3, pp. 265–268, Mar. 1976.

Birger Kaaha, MD, and Melesse Emru, "Promoted Healing of Leprous Ulcers by Transcutaneous Nerve Stimulation," Acupuncture & Electro–Therapeutics Res., Int. J., vol. 13, pp. 165–176, Copyright 1988 Pergamon Press plc.

Mark C. Biedebach, PhD, "Accelerated Healing of Skin Ulcers by Electrical Stimulation and the Intracellular Physiological Mechanics Involved," Acupuncture & Electro–Therapeutics Res., Int. J., vol. 14, pp. 43–60, Copyright 1989 Pergamon Press plc.

Advertisement for Acutron Multiwave for the Optimal Treatment of Myofascial, Joint, and Extremity Injury and Pain, Microcurrent Reasearch, Inc., Copyright 1989–1990 Microcurrent Research, Inc.

Hoffritz Fine Gifts and Cutlery catalog, cover and p. 20 showing The Evaness facial toner, Spring Preview 1990.

Terry Trucco, "Can Electrical Charges Really Stop Wrinkles," The New York Times Comsumer's World, p. 14, Saturday, Aug. 17, 1991.

Copy of advertisement of Lifemax Image II electronic facial toning machine.

The Rejuvenator, copy of web site printout, www.advernet.ie/shapers/rejuvenator.htm, at least as early as Apr. 4, 2001.

* cited by examiner

*Primary Examiner*—Carl Layno
(74) *Attorney, Agent, or Firm*—Law Office of Karen Dana Oster

(57) ABSTRACT

A system for reducing wrinkles on human skin utilizes an electrode to conduct a microcurrent through the surface of the wrinkle into the underlying dermal layer. The electrode is moved in multiple passes along the length of the wrinkle with the electrode in contact with the surface of the wrinkle while generating a periodically repeating microcurrent having a peak amplitude in the range of 10–40 microamps, a peak current density in the range of 10–50 microamps/cm$^2$, and a frequency in the range of 5–15 Hz. The electrode device is self-contained in a battery-containing, cordless case from which a contact electrode protrudes. A hand-engaging second electrode on the surface of the case completes a conductive path through the user's body.

22 Claims, 3 Drawing Sheets

WRINKLE-REDUCING SYSTEM

BACKGROUND OF THE INVENTION

This invention relates to a system for reducing the size of wrinkles on the surface of human skin. More particularly, this invention relates to a system for generating and applying a periodically repeating microcurrent to an elongate wrinkle located on the surface of human skin, thereby inducing changes at the cellular level that result in a perceptible reduction in the size of the treated wrinkle.

The desire to prevent, reduce, or eliminate facial wrinkles has existed for a long time. Even a patent classification exists (U.S. Cl. 128/76 B) entitled "wrinkle eradicators." Prior attempts to reduce or eliminate wrinkles have centered around mechanical devices and chemical treatments. An example of an invention of the mechanical kind is described in Di Matteo, U.S. Pat. No. 3,911,909. That invention was premised on the theory that a wrinkle could be reduced by applying pressure to the exterior of the face and stretching the wrinkled area. Alternatively, devices that mechanically massage the wrinkled area by light vibrations are widely advertised for sale in consumer publications, such as the Evaness™ Cosmetic Treatment device. Chemical treatments are probably best represented by the well-known drug sold under the trademark Retin-A.

The application of electrical currents to various parts of the human body to achieve various therapeutic results is well known. Although how a particular therapeutic result is achieved by the application of an electrical current is not always well understood, electrical currents have been found useful in the following applications:

(1) to help control pain (see Tannenbaum, U.S. Pat. No. 4,233,986, a method and apparatus for the application of 60–125 VAC at 50–150 Hz to the skin adjacent to the painful region);

(2) to help reduce the itching caused by insect bites (see Pierson, U.S. Pat. No. 4,982,743, disclosing approximately 9 VDC applied directly to an insect bite on human skin);

(3) to relieve sinus and nasal congestion (see Claude et al., U.S. Pat. No. 4,926,880, a method and apparatus to generate and apply a square wave of approximately 100–300 microamps to the surface of the skin adjacent to the congested nasal area);

(4) to promote and/or accelerate the healing of skin ulcers (see Gault, low-voltage DC at 200–800 microamps applied directly to skin ulcers);

(5) to promote the healing of soft-tissue wounds in human skin (see Claude, U.S. Pat. No. 4,982,742, a method and apparatus for applying an AC current of from 50–1,000 microamps at a frequency of 10–50 Hz to a soft-tissue wound);

(6) to repair, alter, or reverse different skin conditions, including possibly "smoothing" wrinkles (as reported by the public press); and (7) to electronically stimulate the skin and provide "facial toning" in sit beauty salons and other similar establishments (using such devices as the IMAGE II™, a machine that produces a modified bipolar square wave with a variable frequency and power output to stimulate muscle tissue through multiple hand-held probes or pads applied directly over the muscle).

As can be seen from the above, electrical current has many biomedical applications. The inventor of the present invention is unaware, however, of any previous method or apparatus that has suggested that a periodically repeating microcurrent could be effective only at the dermal cellular level to reduce wrinkles on human skin, or that has suggested how to apply the microcurrent for this purpose.

SUMMARY OF THE INVENTION

The present invention provides a system that enables an individual to safely self-administer a short course of treatment to reduce wrinkles on his or her skin. The design of the device is inherently safe because the voltage and microcurrent generated, and the resultant current density, are very low. This is made possible by the fact that only dermal cells, and not underlying muscle tissue, need be affected to achieve the desired result. Such low microcurrent levels as are insufficient to stimulate muscle tissue are nevertheless sufficient to stimulate blood flow and cellular oxygenation, prevent cellular dehydration, and restore healthy cell regeneration in the dermal layer so as to reduce wrinkles effectively. Overutilization or misapplication of the device will not result in any negative side effects to the user or the device because of the low microcurrent levels involved.

The present invention utilizes a fully self-contained, cordless, single hand-held device that is powered by batteries internally located within the case of the device for microcurrent generation. All the electronics necessary to generate the desired periodic repeating microcurrent are also located within the case of the device. The tip of the device, which constitutes one of its two conductive electrodes, is lightly pressed against, and slowly moved longitudinally in multiple sequential passes along, the surface of the wrinkle that is the subject of the treatment. A current path is completed through the surface of the wrinkle and the underlying dermal layer by the return of the electrons through the subject's body, returning to the device via a hand-engaging second electrode on the device's case. Current flow is preferably generated only if a threshold conductive continuity through the surface of the wrinkle is first sensed. A signal is emitted that alerts the user that threshold continuity is detected and thus that the device is operative.

The foregoing and other objectives, features, and advantages of the invention will be more readily understood upon consideration of the following detailed description of the invention, taken in conjunction with the accompanying drawings.

PREFERRED EMBODIMENT OF THE INVENTION

Figure 1:
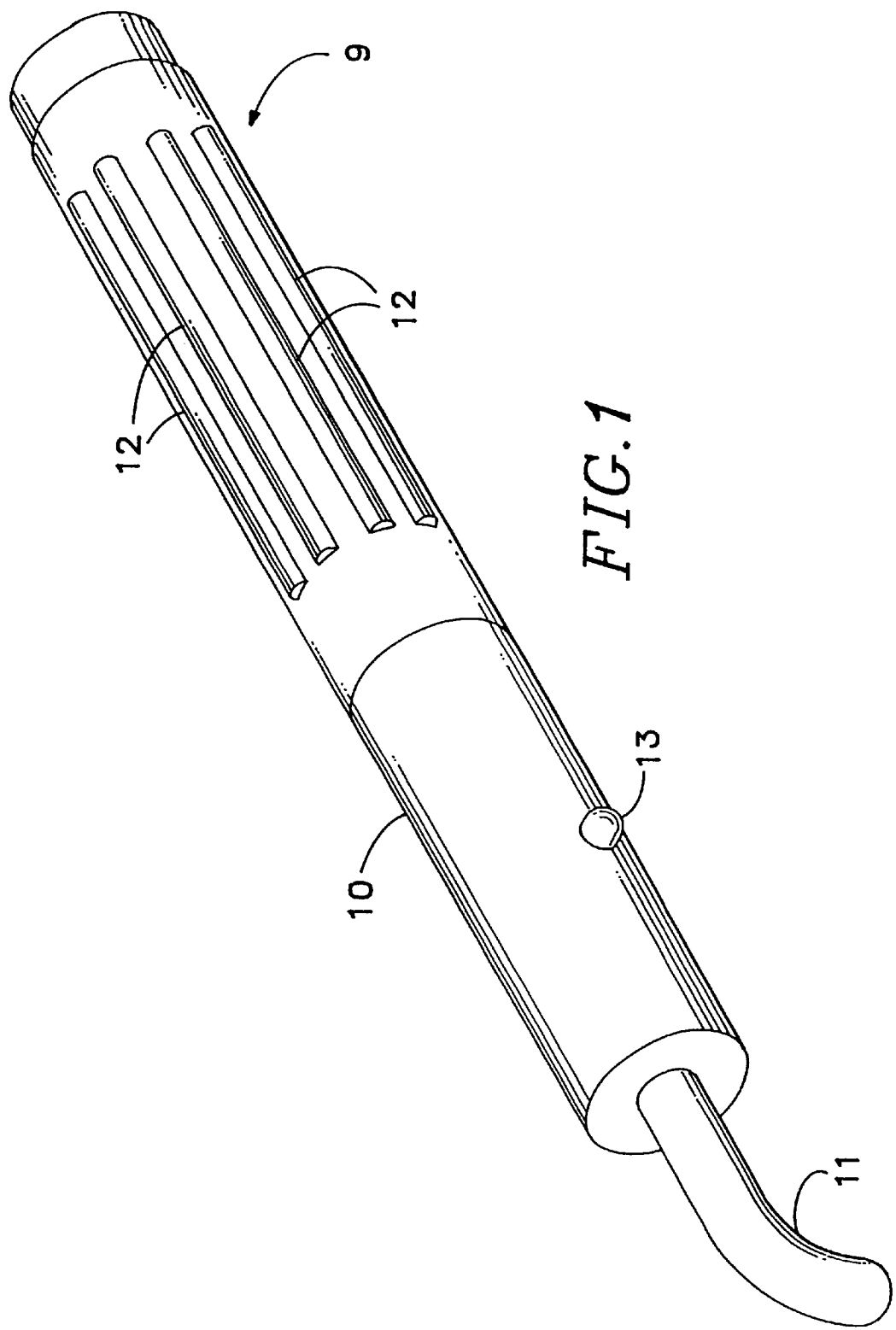
FIG. 1 is a perspective view of a preferred embodiment of the apparatus of the present invention.

With reference to FIG. 1, the exemplary apparatus 9 tof the present invention is composed of an elongate case 10 made of a chemically inert, dielectric material, preferably plastic. All the circuitry and the pair of batteries used to power the circuitry are located internally within the case, which is hermetically sealed.

An electrically conductive first or forward electrode 11 protrudes from one end of the case. This electrode, preferably composed of stainless or surgical steel or other chemically inert conductive material, is about 0.8 cm in diameter, slightly angled, and has a generally smooth hemispherical tip designed to be placed in contact with the surface of a wrinkle on the skin and moved along the length of the wrinkle in multiple sequential passes.

A second or handle electrode 12, insulated from the first electrode 11, is necessary to form a complete circuit, and is created by multiple lengths of a conductive, of preferably chemically inert, material in the form of protruding ribs on the exterior of the case. The protruding rib design of this electrode is aimed at assuring that there is adequate contact between the electrode and the hand of the user when the apparatus is held in the user's hand. The case, or a portion thereof, could alternatively be constructed of a conductive plastic or painted with conductive paint to form the second electrode, provided that the case is insulated from the first electrode.

An L.E.D. 13 is mounted on the exterior of the case and repeatedly flashes OFF and ON only if an adequate threshold conductive path between the two electrodes exists, indicating that the electrical connection between the respective electrodes and corresponding respective portions of the user's skin is sufficiently adequate for the current output of the apparatus 8 to have its intended effect on the skin.

A PREFERRED METHOD OF USING THE EXEMPLARY APPARATUS

A preferred method for using the foregoing apparatus to treat a light facial wrinkle line consists of the following steps:

1. washing the surface of the wrinkle and the area around it and apply a light coating of a conducting cream, e.g., EKG cream, along the length of the wrinkle;
2. holding the apparatus in one clean, bare hand, making sure that the conductive ribs on the case make good contact with the skin of the bare hand;
3. while looking in a mirror, lightly pressing the rounded tip electrode to one end of the surface of the wrinkle to be treated. If the indicator L.E.D. on the case is not blinking, the apparatus is not generating current and the treatment cannot proceed until the user has corrected the problem, which may simply require greater tip contact pressure or repetition of the preceding steps.

If the indicator L.E.D. is blinking, the user should very slowly move the tip along the full length of the wrinkle surface, applying light pressure and maintaining constant contact with the skin. Five or six passes over the wrinkle should be made.

A proposed course of treatment for a light facial wrinkle would consist of performing the steps listed above every two or three days for two to three weeks. If the desired reduction in the wrinkle is achieved, the user may reduce the frequency of the treatment to once or twice a week. It is necessary to continue this abbreviated maintenance schedule of treatment or the wrinkle will return If the wrinkle is not reducing in size, the user should maintain the initial course of treatment before commencing an abbreviated maintenance schedule of treatments.

Below, under a separate subheading, is an overview description of the exemplary electronic apparatus 9 contained inside case 10 of the exemplary apparatus 9, followed by a detailed description of the operation of each particular stage of the electronic apparatus 9.

AN OVERVIEW OF THE ELECTRONIC OPERATION OF THE EXEMPLARY DEVICE

Figure 2:
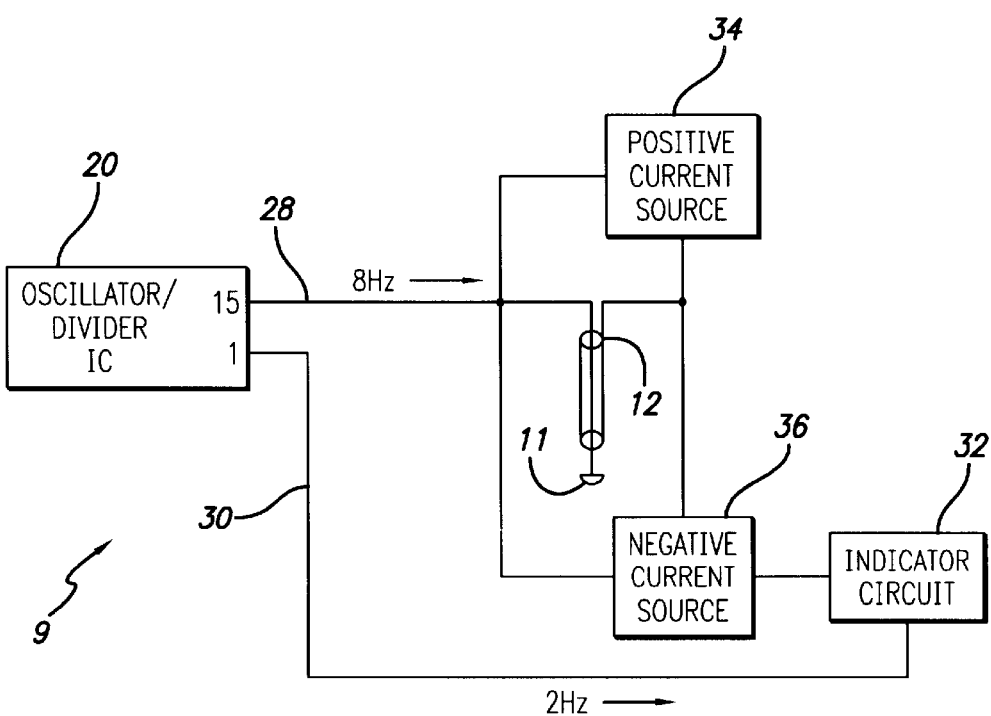
FIG. 2 is a block schematic diagram of the circuit of the preferred apparatus.
Figure 3:
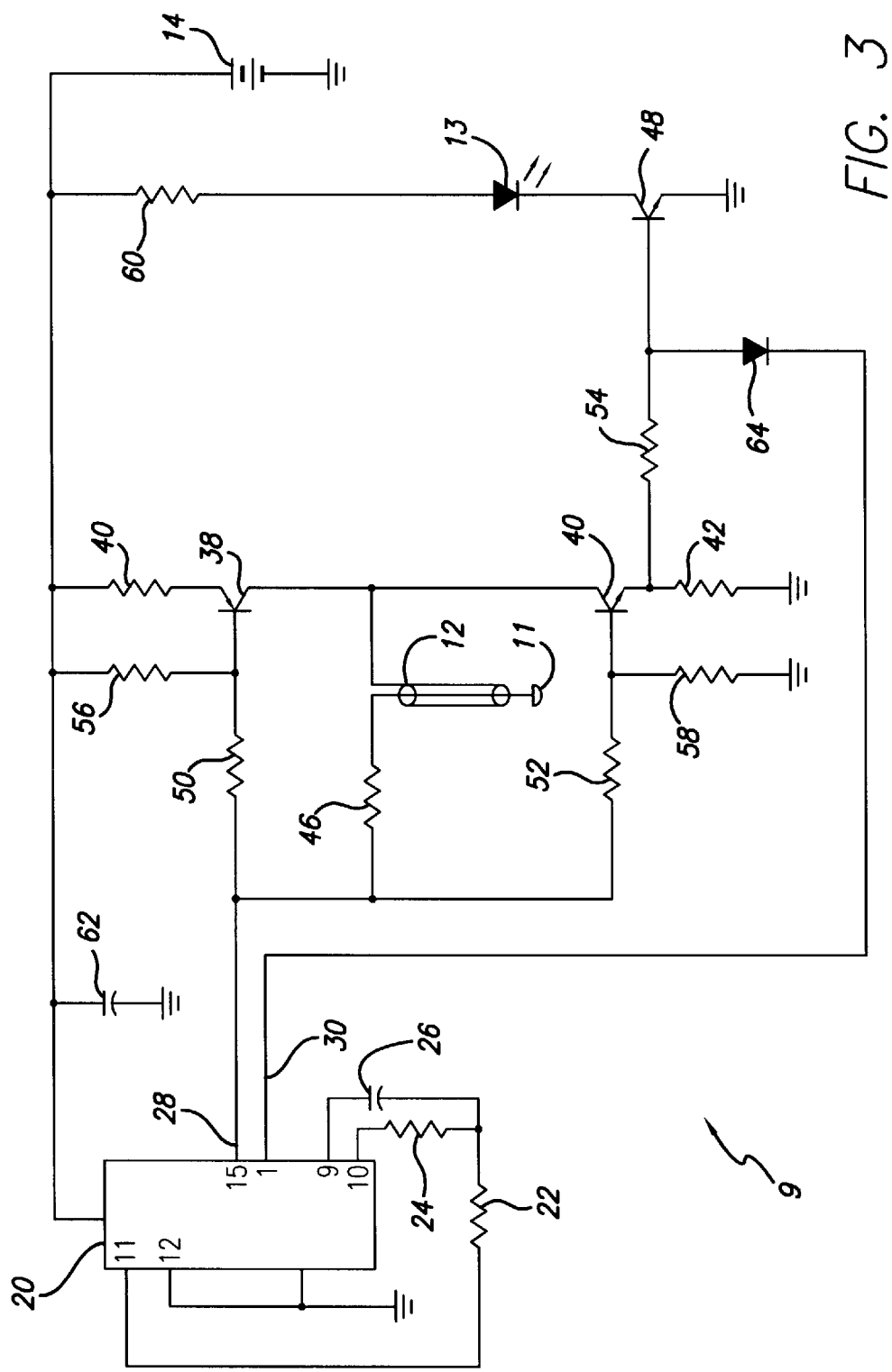
FIG. 3 is a detailed diagram of the circuit of the preferred apparatus.

Referring to FIGS. 2 and 3 together, when the exemplary electronic apparatus 9 is not in contact with the user's skin, that is, when there is no conductive path interposed between the handle electrode 12 and the forward electrode 11, the device is in its idle mode. In this mode, as further explained below, the quiescent current that is drawn from the battery 14 by the exemplary electronic apparatus 9 is from 2 to 10 microamps. The apparatus 9 automatically switches to active mode when the user grasps the handle electrode 12 and touches the forward electrode 11 to a wrinkled site on the skin. During this active mode, the peak value of current supplied is normally about 15 microamps.

DETAILED DESCRIPTION OF THE ELECTRONIC OPERATION OF THE EXEMPLARY DEVICE

With reference, again, to FIGS. 2 and 3, the exemplary electronic apparatus 9 includes an integrated circuit (IC) 20, which is a CMOS oscillator/divider. A suitable device for this purpose is sold commercially by Motorola of Phoenix, Ariz., under the model number listed in Table 2. The oscillator generates an internal frequency of about 8200 Hz. As is well known in the art and described in readily available data sheets, the output frequency of an oscillator/divider integrated circuit may be altered by placing a combination of resistors and capacitors between the pins of the IC. In the exemplary circuit shown, a resistor 22, resistor 24, and capacitor 26 are connected to pins of IC 20 as shown in FIG. 3 so that an 8-Hz square wave output is generated at pin 15 of IC 20, which is then transmitted to the remainder of the circuit via line 28. This 8-Hz square wave alternates between 6 volts and 0 volts. The duration of each voltage excursion is approximately 62.5 milliseconds. The internal circuitry of IC 20 also develops from the original 8200-Hz signal a 2-Hz square wave, which is transmitted by pin 1 of IC 20 to line 30 in order to establish a 2-Hz blink rate for L.E.D. 13 of the indicator circuit 32. In addition to L.E.D. 13, indicator circuit 32 includes a resistor 54, resistor 60, transistor 48, and diode 64. Suitable values or model numbers for these and any other components described herein are listed below in Table 2.

The bipolar microcurrent output of apparatus 9 is generated by two current sources, a positive-going current source 34 and a negative-going current source 36. The positive-going current source 34 comprises a PNP transistor 38 and resistors 44, 50, and 56. The negative-going current source 36 comprises an NPN transistor 40 and resistors 42, 52, and 58. Transistors 38 and 40 are alternately biased off and on by the 8-Hz square wave on line 28. When transistor 38 is on, it acts as a constant current source of 20 microamps for a body resistance of between 0 and 120,000 ohms connected between the electrodes 11 and 12. When transistor 38 is on, the current is of such polarity as to pass from electrode 12 to electrode 11. When transistor 40 is on, the current is of such polarity as to pass from electrode 11 to electrode 12, that is, a negative-going direction from that in which it travels when transistor 38 is on.

The maximum voltage between the electrodes 11 and 12 is about 3.5 volts at any time. The maximum current in the event of a transistor failure is limited by either of resistors 42 or 44 and by resistor 46 to about 35 microamps. The voltages on transistors 38 and 40 as a function of the voltage at pin 15 of IC 20 are given below in Table 1. The transistors 38 and 40 are darlington types so that the forward biased voltage drop that is indicated in Table 1 for each transistor is about 1.3 volts.

TABLE 1

| Condition | O/C/20 Pin 15 | Transistor 38 Base | Transistor 38 Emitter | Transistor 40 Base | Transistor 40 Emitter |
|---|---|---|---|---|---|
| transistor 38 ON | 0 volts | 2.26 volts | 3.66 volts | 0 volts | 0 volts |
| transistor 40 ON | 6 volts | 6 volts | 6 volts | 3.74 volts | 2.3 volts |

Transistor 48 of the indicator circuit 32 acts as a switch for blinking operation of L.E.D. 13. At the base of transistor 48 the 2 Hz squarewave signal from pin 1 of IC 20 is sampled across diode 64 together with the emitter voltage of transistor 40 across resistor 54. When the resistance interposed between electrodes 11 and 12 is within normal values, the emitter voltage of transistor 40 follows the 8 Hz squarewave signal at pin 1 of IC 20, which effectively enables L.E.D. 13 to respond to the 2 Hz squarewave signal so that a 2 Hz blink rate is achieved. Alternatively, if the resistance interposed between electrodes 11 and 12 is unduly large, indicating, for example, that poor electrical contact has been made between apparatus 9 and the user's skin, then the emitter voltage of transistor 40 begins near ground potential. Transistor 48 is then no longer able to switch on positive-going pulses of the 2 Hz squarewave and L.E.D. remains off, thereby signaling to the user the nonoperative condition of apparatus 9.

For the particular model numbers and component values listed in Table 2 below, and taking into account manufacturing-related device variations, the entire circuit will draw less than 10 microamps in its idle mode, and the typical idle mode current drain should be in the range of 2–5 microamps. Because of this minimal current drain in the idle mode, apparatus 9 does not require a Power On switch to conserve the batteries. It is estimated that the batteries will last three years in idle mode or 250 hours in active mode.

When electrodes 11 and 12 are connected to a resistance of 120,000 to 160,000 ohms, about 15 microamps of current are supplied and the current indicator circuit 32 will be triggered on and draw about 1 milliampere of current. For resistances less than 120,000 ohms, the current source will supply about 20 microamps.

Referring to Table 2, exemplary values or model numbers are given for the elements or components depicted in FIG. 3.

TABLE 2

| 22 | 220 | KΩ | 5% | 0.25 W | film |
|---|---|---|---|---|---|
| 24 | 51 | Ω | 5% | 0.25 W | film |
| 46 | 51 | Ω | 5% | 0.25 W | film |
| 50 | 2.0 | MΩ | 5% | — | film |
| 52 | 2.0 | MΩ | 5% | — | film |
| 54 | 2.0 | MΩ | 5% | — | film |
| 56 | 3.3 | MΩ | 5% | 0.25 W | film |
| 58 | 3.3 | MΩ | 5% | 0.25 W | film |
| 42 | 120 | KΩ | 5% | 0.25 W | film |
| 44 | 120 | KΩ | 5% | 0.25 W | film |
| 60 | 680 | Ω | 5% | 0.25 W | film |
| 26 | 1 | µF | 5% | NPO | ceramic |
| 62 | 1 | µF | | tantalum | |
| 20 | | MC14060BAL | | Motorola IC | |
| 38 | | MPSA62 | PNP | darlington | Motorola |
| 40 | | MPSA12 | NPN | darlington | Motorola |
| 13 | | L.E.D. | | Panasonic LN28WAL(US) | |
| 64 | | 1N914 | | diode | |

TABLE 2-continued

| 14 | (2) | 3-volt lithium battery Panasonic BR2330, weight = 0.11 oz size = 0.92" diameter × 0.12" height capacity = 250 milliamphours |
|---|---|---|

While the preferred output of the device is a periodically repeating microcurrent waveform of bipolar, substantially square-wave shape with a peak amplitude of about 15 microamps at a frequency of 8 Hz, good results can be obtained with other waveforms, peak amplitudes, or frequencies. Preferably, however, the current generated should have a peak amplitude substantially in the range of 10–40 microamps and a frequency substantially in the range of 5–15 Hz.

The current output, when referenced to the area of the tip of the electrode 11 that will be placed in contact with the surface of the wrinkle, should preferably produce a peak current density substantially in the range of 10–50 microamps per cm, with a nominal current density of about 30 microamps per cm$^2$.

The terms and expressions that have been employed in the foregoing specification are used as terms of description, not of limitation, and are not intended to exclude equivalents of the features shown and described or portions of them. The scope of the invention is defined and limited only by the claims that follow.

What is claimed is:

1. A method for reducing an elongate wrinkle on human skin, the method comprising the steps of:
    (a) generating a periodically repeating microcurrent through an electrode; and
    (b) conducting said microcurrent through the surface of said wrinkle into the underlying dermal layer of said skin by moving said electrode in multiple sequential passes along the length of said wrinkle with said electrode in conductive contact with said surface of said wrinkle.

2. The method of claim 1, wherein said periodically repeating microcurrent has a peak amplitude greater than 9 microamps.

3. The method of claim 2, wherein said peak amplitude is about 15 microamps.

4. The method of claim 1, further including conducting said periodically repeating microcurrent from said electrode to said surface of said wrinkle at a peak current density greater than 9 microamps/cm$^2$.

5. The method of claim 4 wherein said peak current density is about 30 microamps/cm$^2$.

6. The method of claim 1, further including conducting said periodically repeating microcurrent from said electrode to said surface of said wrinkle at a peak current density less than 51 microamps/cm$^2$.

7. The method of claim 1, wherein said periodically repeating microcurrent has a frequency greater than 4 Hz.

8. The method of claim 7, wherein said frequency is about 8 Hz.

9. The method of claim 1, wherein said periodically repeating microcurrent has a frequency less than 16 Hz.

10. The method of claim 1, wherein said periodically repeating microcurrent has a bipolar wave form.

11. The method of claim 10, wherein said bipolar wave form is substantially square.

12. The method of claim 1, further including completing a conductive path through said surface of said wrinkle by conducting said microcurrent through a hand of the person upon whose skin said wrinkle is located.

13. A self-contained, cordless, hand-held device for reducing a wrinkle on human skin by generating a periodically repeating microcurrent and conducting said microcurrent through the surface of said wrinkle into the underlying dermal layer of said skin, said device comprising:

(a) a first electrode having an electrically conductive tip for contacting the surface of said wrinkle;

(b) a case defining an enclosure from which said first electrode protrudes, and having a second electrode thereon insulated from said first electrode for contacting a human hand when said hand grasps said case; and (c) circuitry located within said case for generating said periodically repeating microcurrent, including a battery located within said case for powering said circuitry;

(d) wherein said circuitry includes means for generating said periodically repeating microcurrent at a frequency less than 16 Hz.

14. The apparatus of claim 13, wherein said second electrode is composed of a chemically inert conductive material.

15. The apparatus of claim 13, wherein said circuitry includes means for generating said periodically repeating microcurrent at a peak amplitude greater than 9 microamps.

16. The apparatus of claim 15, wherein said peak amplitude is about 15 microamps.

17. The apparatus of claim 13, wherein said circuitry includes means for generating said periodically repeating microcurrent at a peak amplitude less than 41 microamps.

18. The apparatus of claim 13, wherein said circuitry includes means for generating said periodically repeating microcurrent at a frequency greater than 4 Hz.

19. The apparatus of claim 18, wherein said frequency is about 8 Hz.

20. The apparatus of claim 13, wherein said circuitry includes means for generating said periodically repeating microcurrent as a bipolar wave form.

21. The apparatus of claim 20, wherein said bipolar wave form is substantially square.

22. A self-contained, cordless, hand-held device for reducing a wrinkle on human skin by generating a periodically repeating microcurrent and conducting said microcurrent through the surface of said wrinkle into the underlying dermal layer of said skin, said device comprising:

(a) a first electrode having an electrically conductive tip for contacting the surface of said wrinkle;

(b) a case defining an enclosure from which said first electrode protrudes, and having a second electrode thereon insulated from said first electrode for contacting a human hand when said hand grasps said case; and (c) circuitry located within said case for generating said periodically repeating microcurrent, including a battery located within said case for powering said circuitry;

(d) wherein said circuitry includes means for generating said periodically repeating microcurrent at a frequency of about 8 Hz.

* * * * *